US006231586B1

(12) United States Patent
Mariant

(10) Patent No.: US 6,231,586 B1
(45) Date of Patent: May 15, 2001

(54) THREE DIMENSIONAL IN-FILLING VASO-OCCLUSIVE COILS

(75) Inventor: Michael J. Mariant, San Jose, CA (US)

(73) Assignee: Target Therapeutics, Inc., Fremont, CA (US)

(*) Notice: Under 35 U.S.C. 154(b), the term of this patent shall be extended for 0 days.

(21) Appl. No.: 09/389,914

(22) Filed: Sep. 3, 1999

Related U.S. Application Data

(62) Division of application No. 08/845,815, filed on Apr. 29, 1997, now Pat. No. 5,957,948, which is a continuation of application No. 08/467,403, filed on Jun. 6, 1995, now Pat. No. 5,624,461.

(51) Int. Cl.[7] .................................................. A61B 17/32
(52) U.S. Cl. ............................................................ 606/191
(58) Field of Search ..................................... 606/191, 198, 606/200, 194, 151, 158

(56) References Cited

U.S. PATENT DOCUMENTS

| 3,174,851 | 3/1965 | Buehler et al. . |
| 3,351,463 | 11/1967 | Rozner et al. . |
| 3,753,700 | 8/1973 | Harrison et al. . |
| 4,994,069 | 2/1991 | Ritchart et al. . |
| 5,122,136 | 6/1992 | Guglielmi et al. . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,304,194 | 4/1994 | Chee et al. . |
| 5,304,195 | 4/1994 | Twyford, Jr. et al. . |
| 5,312,415 | 5/1994 | Palermo . |
| 5,350,397 | 9/1994 | Palermo et al. . |
| 5,354,295 | 10/1994 | Guglielmi et al. . |
| 5,382,259 | 1/1995 | Phelps et al. . |
| 5,536,274 | 7/1996 | Neuss . |
| 5,645,558 | 7/1997 | Horton . |
| 5,690,666 | 11/1997 | Berenstein et al. . |
| 5,911,731 | * 6/1999 | Pham et al. ........................ 606/191 |

FOREIGN PATENT DOCUMENTS 3 203 410 A1  11/1982 (DE) .
WO 92/14408   9/1992 (WO) .

* cited by examiner

Primary Examiner—Michael Buiz
Assistant Examiner—Vy Q. Bui
(74) Attorney, Agent, or Firm—Morrison & Foerster LLP

(57) ABSTRACT

This is an implantable vaso-occlusive device. It is a complex, helically wound coil comprised of a primary helically wound coil which is then wound into a specific secondary shape. The final shape upon deployment is in the approximate shape of an anatomical cavity. upon deployment, the device first fills the periphery of the cavity and then continues to infill the center. The device is a self-forming shape made from a pre-formed linear helically wound. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action. The invention also includes methods of winding the vaso-occlusive device into appropriately shaped forms and annealing them.

9 Claims, 3 Drawing Sheets

THREE DIMENSIONAL IN-FILLING VASO-OCCLUSIVE COILS

This application is a divisional of U.S. Ser. No. 08/845,815, filed Apr. 29, 1997, now U.S. Pat. No. 5,957,948, which is a continuation of U.S. Ser. No. 08/467,403, filed Jun. 6, 1995, now U.S. Pat. No. 5,624,461 the contents of which are hereby incorporated by reference into the present disclosure.

FIELD OF THE INVENTION

This invention is an implantable vaso-occlusive device. It is a complex, helically wound coil comprised of a primary helically wound coil which is then wound into a specific secondary shape. The final shape upon deployment is in the approximate shape of an anatomical cavity. Upon deployment, the device first fills the periphery of the cavity and then continues to infill the center. The device is a self-forming shape made from a pre-formed linear helically wound. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action. The invention also includes methods of winding the vaso-occlusive device into appropriately shaped forms and annealing them.

BACKGROUND OF THE INVENTION

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Vaso-occlusive coils having little or no inherent secondary shape have also been described. For instance, in U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

None of these devices are self-forming helical coils which first fill the periphery of a vascular space upon ejection from a delivery catheter.

SUMMARY OF THE INVENTION

This invention is a vaso-occlusive device comprising one or more vaso-occlusive helical coils which are formed by winding a wire into a first helix; the first helix is then wound into a secondary form. The secondary form is one which, when ejected from a delivery catheter, forms a generally spherical shape, filling first the outer periphery of the spherical shape and then the center region. Desirably, the vaso-occlusive device is of a size and shape suitable for fitting snugly within a vascular cavity (e.g., an aneurysm, or perhaps, a fistula). The stiffness of the various parts of the coil may be selected to enhance the utility of the device for specific applications. Fibrous materials may be woven into the member or tied or wrapped onto it.

The device may be made in a variety of ways. Typically, the member is helically wound in a generally linear fashion to form a first or primary winding. After completion of that step, the primary winding is then wound around a first appropriately shaped winding fixture or form and the assembly heat-treated to help it retain its shape after removal from the winding fixture. Auxiliary fibrous materials are then added by weaving, tying, or other suitable permanent attachment methods.

The device is used simply by temporarily straightening the device and introducing it into a suitable catheter, the catheter already having been situated so that its distal opening is within the mouth of the vascular cavity or opening to be filled. The device is then pushed through the catheter and, upon its ejection from the distal end of the catheter into the vascular cavity, assumes its relaxed shape.

The device is typically used in the human vasculature to form emboli but may be used in any site in the human body where an occlusion such as one produced by the inventive device is needed.

DESCRIPTION OF THE INVENTION

This invention is a vaso-occlusive device comprising one or more vaso-occlusive helical coils which are formed by winding a wire into a first helix; the first helix is then wound into a secondary form. The secondary form is one which, when ejected from a delivery catheter, forms a generally spherical shape, filling first the outer periphery of the spherical shape and then the center region. Desirably, the vaso-occlusive device is of a size and shape suitable for fitting snugly within a vascular cavity (e.g., an aneurysm, or perhaps, a fistula).

Figure 1A:
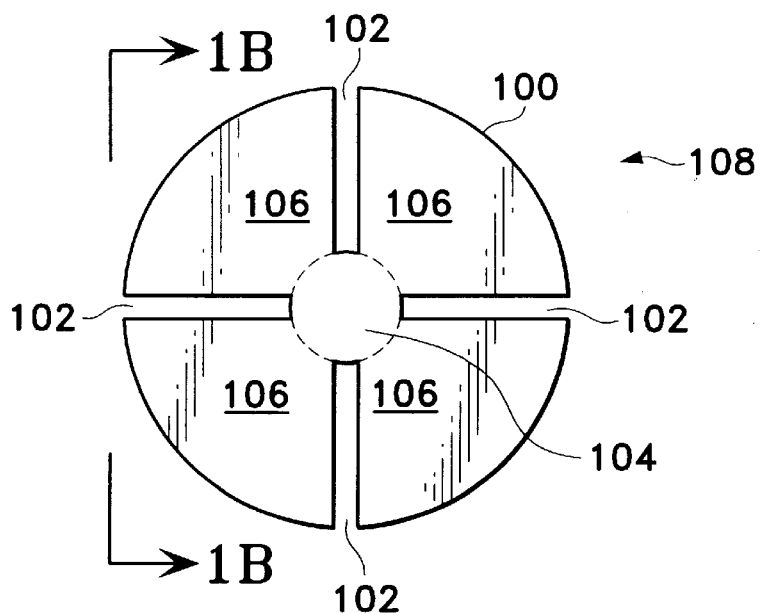
FIG. 1A shows an end view of a winding mandrel for constructing vaso-occlusive coils made according to the invention.

FIG. 1A shows an end view of a mandrel used to wind vaso-occlusive devices according to the invention. It is this pattern of winding which provides the benefit of the invention at deployment. The end view shows a circular form (100) having four slots cut form the periphery of the circular form to the center support. This results in a form having four "poles" (106) upon which the inventive vaso-occlusive coils are wound. A single form such as is viewed in the FIG. 1A perspective is sufficient to produce a single vaso-occlusive device. However, it is desirable to "gang" such plates together in an assembly (108) such as is shown in FIG. 1B to allow simultaneous production and heat treatment of multiple such devices.

The winding mandrel (108) should be of sufficient heat resistance to allow a moderate annealing step. The mandrel may be made of a refractory material such as alumina or zirconia (for heat-treating devices made of purely metallic components) or may be made of a metallic coil material. The function of the mandrel is simply to form a support for winding, not pollute the device during the heat-treatment step, and provide a specific form to the device during that heat-treatment step. A typical annealing step for a platinum/tungsten alloy coil would involve a 1100° F. heating step in air for about 15–20 minutes.

Figure 1B:
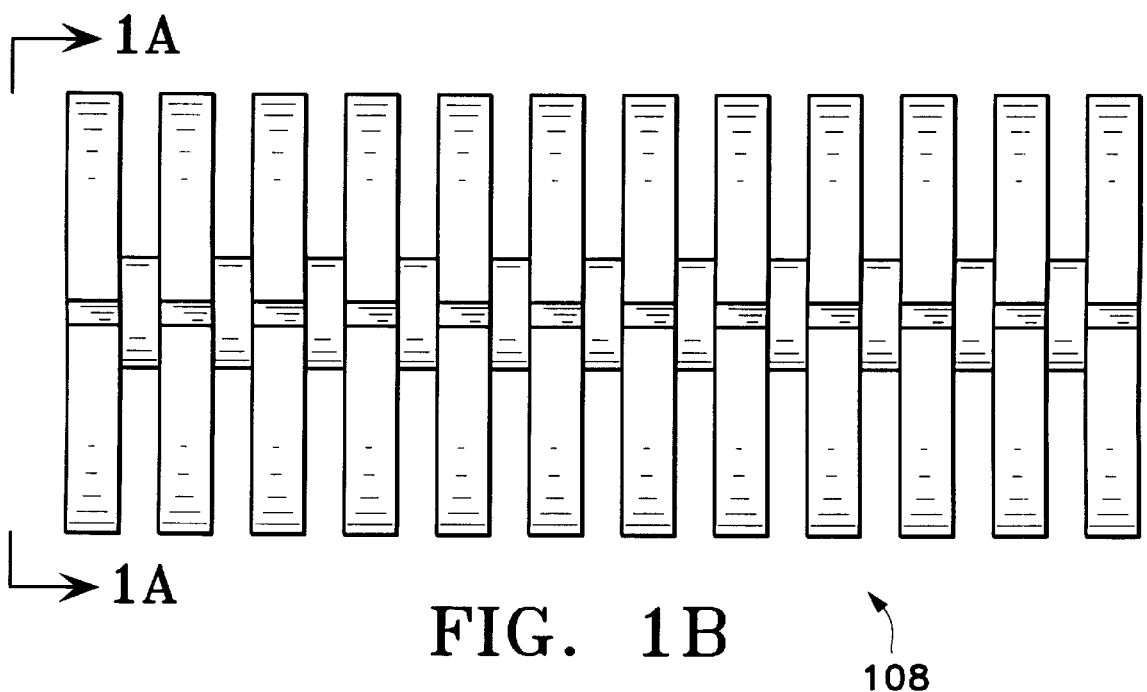
FIG. 1B shows a side view of the winding mandrel of FIG. 1A.
Figure 2A:
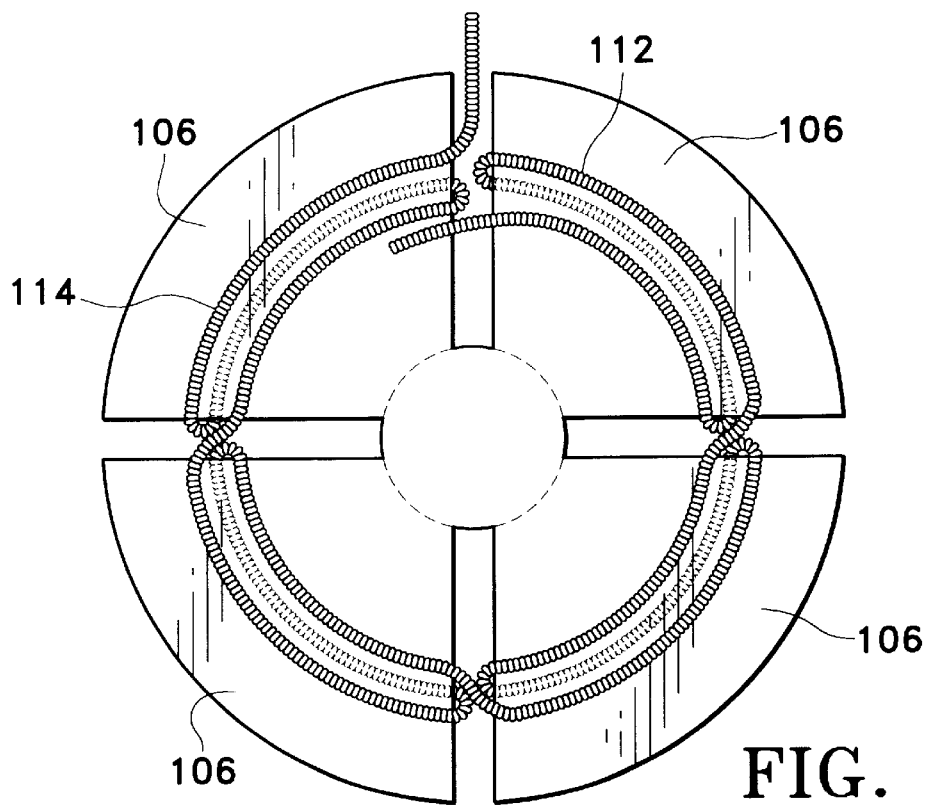
FIG. 2A shows an end view of the winding mandrel of FIG. 1A with a primary coil wound on the mandrel.

FIG. 2A shows an end view of the winding mandrel of FIGS. 1A and 1B with a coil wound upon it. The sequence of winding is relatively important to this invention.

First of all, however, the material used in constructing the vaso-occlusive member may be any of a wide variety of materials; preferably, the wire is a radio-opaque material such as a metal or a polymer. Suitable metals and alloys for the wire making up the primary coil (112) include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire.

If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like.

The coil material is first wound into a primary coil (112). The primary coil is typically linear after it has been wound and annealed. Generally speaking, when the device (114) is formed of a metallic coil and that coil is a platinum alloy or a superelastic alloy such as nitinol, the diameter of the wire used in the production of the coil will be in the range of 0.0005 and 0.006 inches. The wire of such diameter is typically then wound into a primary coil (112) having a primary diameter of between 0.005 and 0.025 inches. For most neurovascular indications, the preferable diameter is 0.010 to 0.018 inches. We have generally found that the wire may be of sufficient diameter to provide a hoop strength to the resulting device sufficient to hold the device in place within the chosen body cavity without distending the wall of the cavity and without moving from the cavity as a result of the repetitive fluid pulsing found in the vascular system.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Figure 2B:
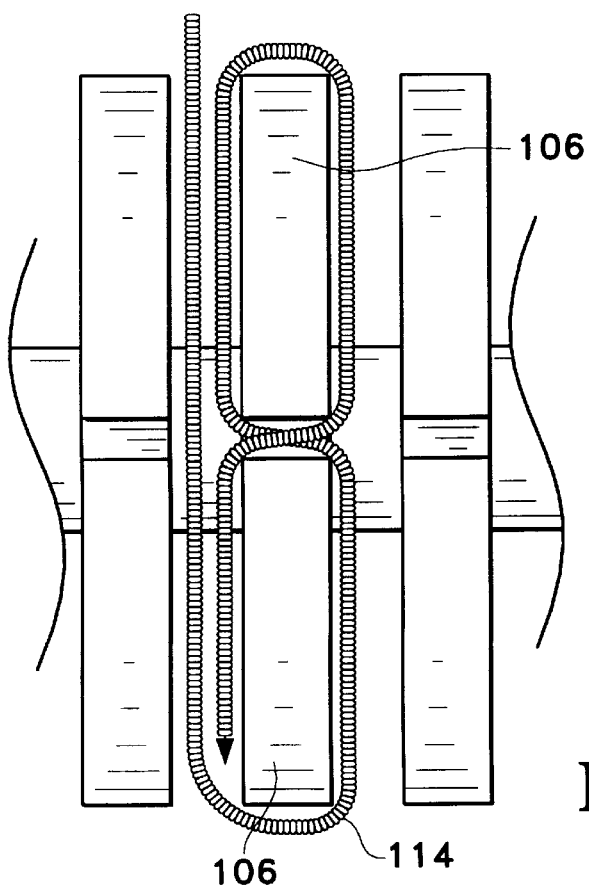
FIG. 2B shows a side view of the winding mandrel cum vaso-occlusive coil of FIG. 2A.

The primary coil (112) is then sequentially wound on each of the poles (106) beginning at the inner radius and progressing outwardly. The side view of the path of the winding path for device (114) is shown in FIG. 2B. This may be considered as a series of wound sections, each of which section is wound in a decreasing diameter.

Although the set of four wound poles is considered to be a complete device according to the invention, such is not required. The device may be of more or less segments, as designed.

Once the device is completely wound, the assembly of mandrel and coil is then subjected to an annealing step such as that discussed above.

The overall diameter of the device (114) as deployed is generally between 3 and 12 millimeters. Most aneurysms within the cranial vasculature can be treated by one or more devices having those diameters. Of course, such diameters ar not a critical aspect of the invention.

Also contemplated in this invention is the attachment of various fibrous materials to the inventive coil (114) for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

The coil is then removed from the winding mandrel and loaded into a carrier for introduction into the delivery catheter. It is important to the efficient functioning of the invention that a portion of the coil which was wound on an outer radius of a pole (106) be the leading or distal section of coil as it is delivered.

Figure 3A:
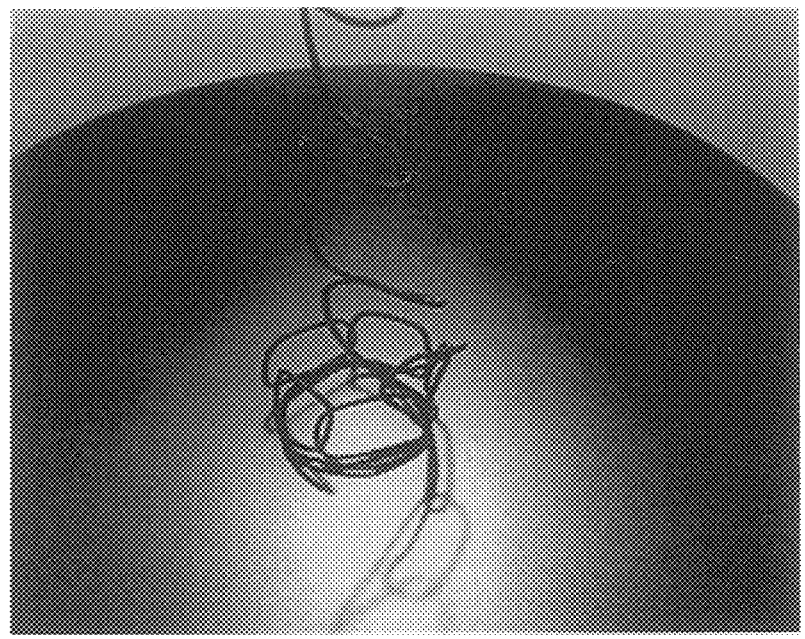
FIG. 3A is a photograph of the initial deployment of the inventive coil showing the "shell" formed during initial deployment.
Figure 3B:
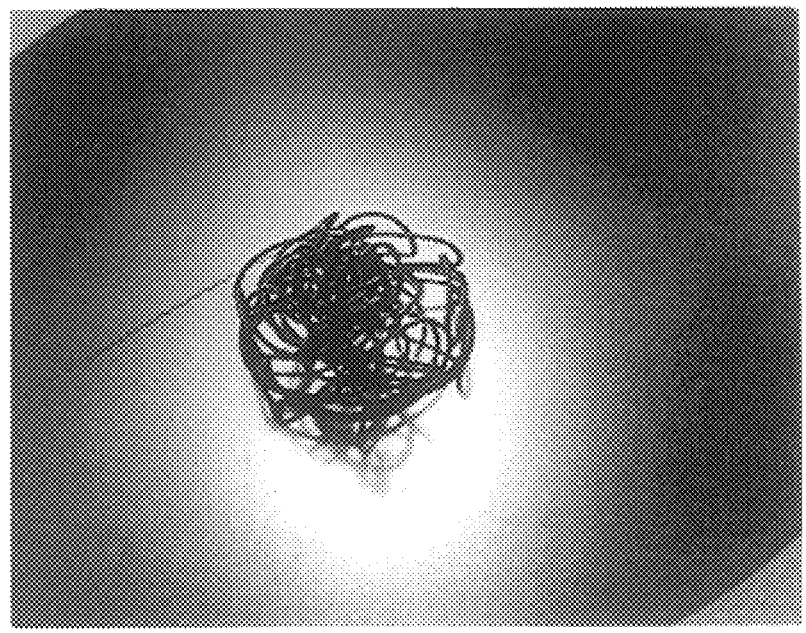
FIG. 3B is a photograph of the final deployment of the inventive coil showing the relatively spherical shape formed during that complete deployment.

FIG. 3A is a photograph of an inventive coil at an early stage of its deployment. The outer periphery of the partially deployed device is seen at the upper end of the photograph. FIG. 3B is a photograph of a completely deployed device made from a set of four poles (see, FIG. 2A, 106) on a winding mandrel. These coils were constructed from a platinum alloy having 8% tungsten.

Modification of the above-described variations of carrying out the invention that would be apparent to those of skill in the fields of medical device design generally, and vaso-occlusive devices specifically, are intended to be within the scope of the following claims.

What is claimed is:

1. A method of making a vaso-occlusive device comprising:
   a) winding a wire into a helical form;
   b) winding the helical wire formed in step a) onto a circular mandrel having four slots;
   c) heating the helical wire on the mandrel to form a coil having a secondary form; and
   d) removing the coil from the winding mandrel.

2. The method according to claim 1 wherein the wire is a metal selected from the group consisting of platinum, palladium, rhodium, gold, tungsten, and their alloys.

3. The method according to claim 2 wherein the wire is an alloy of platinum and tungsten.

4. The method according to claim 1 wherein the heating step is an annealing step.

5. The method according to claim 1 wherein the mandrel comprises a refractory material.

6. The method according to claim 5 wherein the the refractory material comprises alumina or zirconia.

7. The method according to claim 1 wherein the mandrel comprises a metal selected from the group consisting of platinum, palladium, rhodium, gold, tungsten and their alloys.

8. The method according to claim 1 wherein the helical wire step b) is performed such that the wire overlaps itself at each of the mandrel's slots.

9. The method according to claim 1 wherein the mandrel comprises more than one circular mandrel section having four slots.

* * * * *